US00PP13235P2

(12) United States Plant Patent
Utecht

(10) Patent No.: US PP13,235 P2
(45) Date of Patent: Nov. 19, 2002

(54) GERANIUM PLANT NAMED 'FISTADOR'

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 09/323,149

(22) Filed: Jun. 1, 1999

(51) Int. Cl.[7] ..... A01H 5/00
(52) U.S. Cl. ..... Plt./330
(58) Field of Search ..... Plt./330, 325

(56) References Cited

FOREIGN PATENT DOCUMENTS

| | | |
|---|---|---|
| PL | 475 | 12/1998 |
| CA | 98-1366 | 4/1998 |
| CH | 98-26-1425 | 4/1998 |
| DE | PEL 1014 | 6/1994 |
| EP | 96/0419 | 3/1996 |

OTHER PUBLICATIONS

UPOV–ROM GTIM Computer Database 1999/02, GTI Jouve Retrieval Software, citation for 'Fistador', 1994–1998.*
Licensing agreement for 'Fisrosimo', http://www.sicasov.com/baremes/f–fl9899.htm, 1998–1999.*
Kessler, Greenhouse Production of Zonal Geranium, http://www.aces.edu/department/extcomm/publications/anr/anr–1106/anr–1106.htm, Apr. 1998.*
Pelargonium 1998, Pelfi Fischer, Hillscheid Germany, p. 7 (1998/1999).

* cited by examiner

*Primary Examiner*—Bruce R. Campell
*Assistant Examiner*—Anne Marie Grünberg
(74) *Attorney, Agent, or Firm*—Foley & Lardner

(57) ABSTRACT

A new and distinct cultivar of geranium plant named 'Fistador', as described and illustrated, and particularly characterized by the combined features of scarlet, cup-shaped flowers; medium-sized semi-spherically shaped inflorescence; intense green foliage with distinct zonation; and medium-tall, well-branched and rounded plant habit.

1 Drawing Sheet

BACKGROUND OF THE INVENTION

The present invention comprises a new and distinct cultivar of geranium plant, botanically known as *Pelargonium zonale*, and hereinafter referred to by the cultivar name 'Fistador'.

'Fistador' is a product of a planned breeding program which had the objective of creating new geranium varieties with red flower color, medium green, zoned foliage, and medium sized plant habit.

'Fistador' was originated from a hybridization made by the inventor, Angelika Utecht, in a controlled breeding program in Galdar, Gran Canaria, Spain, in 1991. The female parent was the cultivar 'Fisnida' (unpatented), characterized by single-shaped florets, orange-red flowerheads on strong peduncles, medium green, zoned foliage, and vigorous growth. The male parent of 'Fistador' was the commercial variety 'Robe', having dark cherry-red, semi-double flowers, light to medium green foliage with weak zonation, and compact plant habit.

'Fistador' was selected as one flowering plant within the progeny of the stated cross by the inventor, Angelika Utecht, in 1992 in a controlled environment in Galdar, Gran Canaria, Spain.

The first act of asexual reproduction of 'Fistador' was accomplished when vegetative cuttings were taken from the initial selection in autumn 1992 in a controlled environment in Galdar, Gran Canaria, Spain by Angelika Utecht. Horticultural examination of plants grown from cuttings of the clone, initiated in May 1993 in Hillscheid, Federal Republic of Germany, and continuing thereafter, has demonstrated that the combination of characteristics as herein disclosed for 'Fistador' are firmly fixed and are retained through successive generations of asexual reproduction.

BRIEF DESCRIPTION OF THE INVENTION

The following traits have been repeatedly observed and are determined to be basic characteristics of 'Fistador', which in combination distinguish this geranium as a new and distinct cultivar:

1. Scarlet to orange-red semi-double flowers;

2. Semi-spherically shaped inflorescence;

3. Medium green foliage with distinct zonation;

4. Medium sized plant habit, relatively compact during cultivation, fairly vigorous growth outdoors; and 5. Early to medium flowering response.

'Fistador' has not been observed under all possible environmental conditions. The phenotype of the new cultivar may vary significantly with variations in environment such as temperature, light intensity and daylength without any change in the genotype of the plant. The following observations, measurements, and comparisons describe plants grown in Hillscheid, Germany, and in Langley, British Columbia, Canada, under greenhouse conditions which approximate those generally used in commercial practice.

Of the many commercial cultivars known to the present inventor, the most similar in comparison to 'Fistador' is the related cultivar 'Fissamba' (U.S. Plant Pat. No. 10,364). In comparison to 'Fissamba', 'Fistador' has a slightly lighter, more orange-red or scarlet shade of flower color, somewhat differently shaped inflorescence (wider, semi-spherical, not spherical), weaker anthocyanin (reddish) coloring of pedicels and sepals, slightly stronger zonation, somewhat stronger growth and more rounded, lower and wider plant habit.

BRIEF DESCRIPTION OF THE DRAWING

The accompanying color photographic drawing shows typical flower and foliage characteristics of 'Fistador' with colors being as true as possible will illustrations of this type.

DETAILED BOTANICAL DESCRIPTION

The measurements were taken in Langley, British Columbia, Canada, on May 26, 1998, 10 weeks after planting of rooted cuttings into 15-cm pots. The plants had not been pinched. In the following description, color references are made to The Royal Horticultural Society Colour Chart (R.H.S.). The color values were determined indoors from flowers developed in a greenhouse in May 1998 in Hillscheid, Germany.

CLASSIFICATION

Botanical: A hybrid of the species *Pelargonium zonale L'Hérit.*

Commercial: Zonal geranium, cv. 'Fistador'.

INFLORESCENCE

Umbel:

*Shape.*—Semi-spherical.

*Average diameter.*—98 mm.

*Average depth.*—60 mm.

*Peduncle length.*—145 mm.

*Peduncle color.*—Light green. RHS 143 B, no anthocyanin.

*Peduncle texture.*—Slightly rough or velvety, due to the dense, short pubescence.

*Pedicel length.*—21 mm.

*Pedicel color.*—Mainly light-green, RHS 144 A, reddish/brownish color at the upper end is RHS 179 A–RHS 179 B.

*Number of flowers per umbel.*—Approximately 30.

*Lastingness of the individual umbel.*—Medium-sized, with individual flowers in various stages of development, persistence is about average for zonal varieties, lasting approximately 18 days in greenhouse conditions in spring at a minimum temperature of 18° C.

Corolla:

*Average diameter.*—46 mm.

*Form.*—Semi-double.

*Shape.*—Nearly round, cup-shaped, open in the middle.

*Number of petals.*—7–9.

*Number of petaloids.*—0–2.

*Color of petaloids.*—RHS 43 A.

*Color (general tonality from a distance of three meters).* —Scarlet.

*Color of upper petals.*—RHS 40 A–43 A.

*Markings of upper petals.*—Very weak dark-red veins, closest to RHS 59A.

*Color of lower petals.*—RHS 43 A.

*Color of lower surface of petals.*—RHS 44 C–46 C.

*Color of sepals.*—Green, RHS 143 A–B, small reddish/brownish, RHS 179 A–RHS 179 B, spots at the bases.

*Number of sepals.*—5.

*Texture of sepals.*—Smooth, with hardly any pubescence.

Bud (just before petals unfold):

*Shape.*—Broad and elliptical.

*Color (sepals).*—Medium green, RHS 143 A–B.

*Color (petals).*—Red to cherry-red, approximately RHS 45 B.

*Length.*—Approximately 17 mm.

*Width.*—Approximately 11 mm.

Reproductive organs:

*Androecium.*—Usually 7 fertile anthers, filaments are mainly white and pink at the upper end, the pollen is yellow-orange.

*Gynoecium.*—5–6-lobed stigma, red stigma and style, RHS 44 A.

*Fertility/seed set.*—Occasionally, a few seeds are developed.

Spring flowering response period: In Hillscheid, Germany, in 1998, plants had on average 0.7 flowers opened 11 weeks after planting of unrooted cuttings.

Outdoor flower production: Medium number of inflorescence, continuously flowering.

*Blooming habit.*—Continuous flowering from about May to mid-September; after which flowering may be poor depending on general conditions and light intensity. There is no noticeable fragrance apart from the slightly aromatic scent that can be noticed when flowers are crushed.

Durability: Good shatter resistance, good rain resistance, less susceptible to 'burning' of flowers in sunny periods than many red flowered varieties.

PLANT

Foliage:

*Form.*—Kidney-shaped with an open base.

*Margin.*—Bicrenated.

*Texture.*—Slightly velvety and dull (not glossy).

*Size of leaf.*—81 mm.

*Color of upper surface.*—Medium green, approximately RHS 137 B–C.

*Color of lower surface.*—RHS 137 D.

*Color of zonation.*—Brown, approximately RHS 166 A, distinctness is 5 (in the range from 1="no zonation" to 9="very strong").

*Tolerance of botrytis.*—Average.

General appearance and form:

*Internode length.*—5–20 mm.

*Branching pattern.*—6.3 naturally-occurring branches.

*Size of foliage.*—14.5 cm high and 33.0 cm in diameter.

I claim:

1. A new and distinct cultivar of geranium plant named 'Fistador', as described and illustrated.

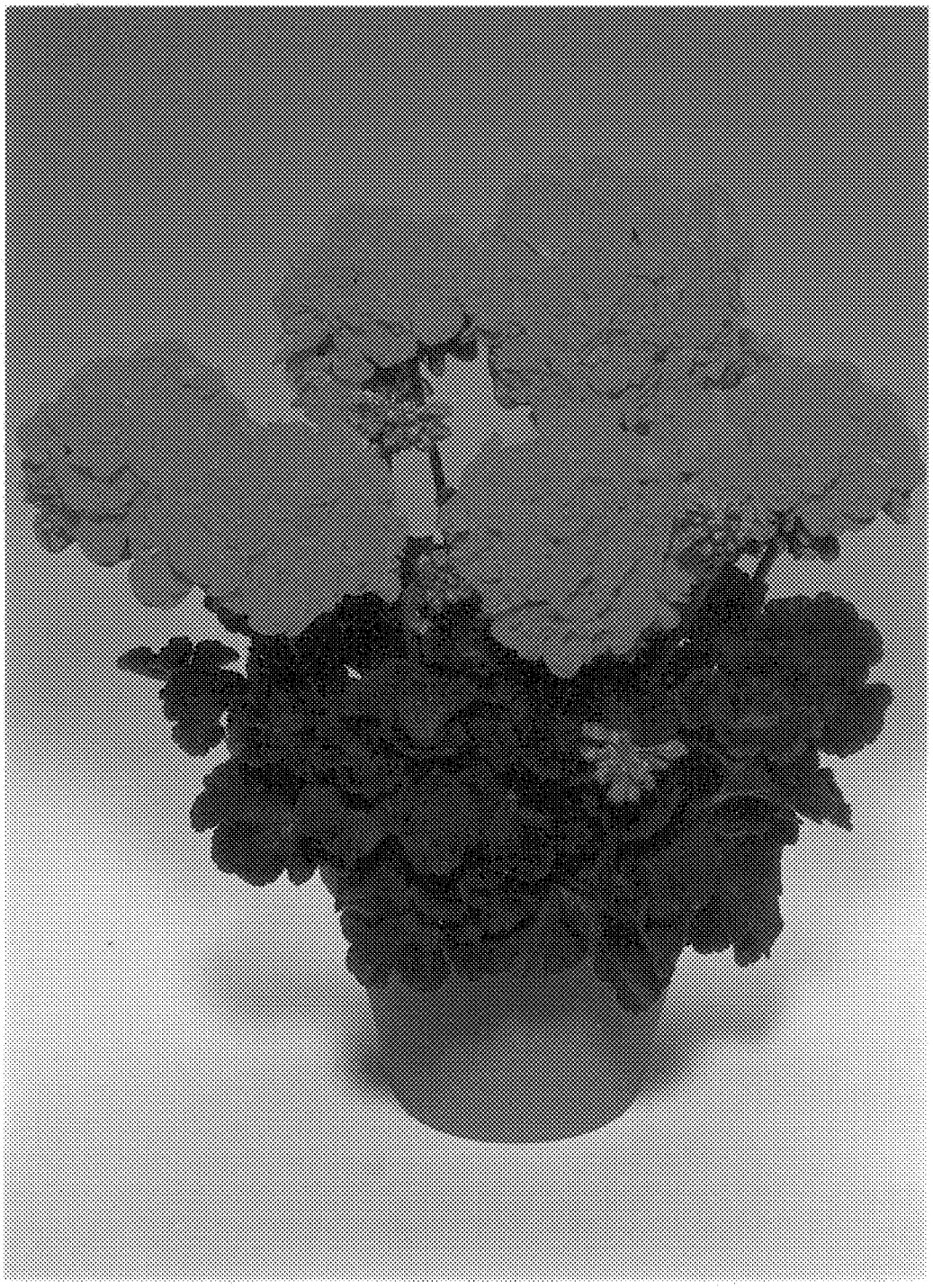

* * * * *